United States Patent
Rubin et al.

(10) Patent No.: US 11,376,291 B2
(45) Date of Patent: Jul. 5, 2022

(54) BENEFICIAL GROWTH AND CONSTITUENTS OF MUSHROOMS ON SUBSTRATE CONTAINING CANNABIS PLANT MATERIAL

(71) Applicant: Functional Fungi, LLC, Arroyo Grande, CA (US)

(72) Inventors: Jordan Seth Rubin, Koshkonong, MT (US); Andrew Hines Miller, Calistoga, CA (US)

(73) Assignee: BYO Holdings, LLC, Kosh Konong, MO (US)

(*) Notice: Subject to any disclaimer, the term of this patent is extended or adjusted under 35 U.S.C. 154(b) by 144 days.

(21) Appl. No.: 15/367,807

(22) Filed: Dec. 2, 2016

(65) Prior Publication Data

US 2017/0296602 A1  Oct. 19, 2017

Related U.S. Application Data

(60) Provisional application No. 62/263,309, filed on Dec. 4, 2015.

(51) Int. Cl.
| | | |
|---|---|---|
| *A61K 36/07* | (2006.01) | |
| *A61K 36/185* | (2006.01) | |
| *A01G 18/66* | (2018.01) | |
| *A01G 18/20* | (2018.01) | |
| *A01G 18/30* | (2018.01) | |
| *A61K 31/352* | (2006.01) | |
| *A61K 31/05* | (2006.01) | |
| *A23L 19/00* | (2016.01) | |
| *A23L 31/00* | (2016.01) | |
| *A23L 29/00* | (2016.01) | |

(52) U.S. Cl.
CPC .............. *A61K 36/07* (2013.01); *A01G 18/20* (2018.02); *A01G 18/30* (2018.02); *A01G 18/66* (2018.02); *A23L 19/03* (2016.08); *A23L 29/00* (2016.08); *A23L 31/00* (2016.08); *A61K 31/05* (2013.01); *A61K 31/352* (2013.01); *A61K 36/185* (2013.01); *A23V 2002/00* (2013.01)

(58) Field of Classification Search
CPC ...... A61K 36/06; A61K 36/07; A61K 31/352; A61K 36/00; A61K 36/185; A23L 31/00
See application file for complete search history.

(56) References Cited

FOREIGN PATENT DOCUMENTS

| CN | 103449906 A | * | 12/2013 | |
|---|---|---|---|---|
| CN | 103787700 A | * | 5/2014 | |
| WO | WO-2005067581 A2 | * | 7/2005 | ............. A01G 18/00 |

OTHER PUBLICATIONS

Growing Mycelium on Marijuana. Internet Posting Date: Dec. 12, 2005. Retrieved from the Internet on: Feb. 21, 2020. Retrieved from: <URL: https://www.shroomery.org/forums/showflat.php/Number/5051048>. (Year: 2005).*

* cited by examiner

*Primary Examiner* — Amy L Clark
(74) *Attorney, Agent, or Firm* — Barbara E Johnson, Esq.

(57) ABSTRACT

A process for growing mycelium with cannabis, by designing and filling a spawn bag with medium containing cannabis, water and optional grain, followed by inoculating and maturing mycelium spawn to grow and harvest mushrooms with optional drying thereafter.

3 Claims, No Drawings

BENEFICIAL GROWTH AND CONSTITUENTS OF MUSHROOMS ON SUBSTRATE CONTAINING CANNABIS PLANT MATERIAL

This nonprovisional patent application claim priority to, and hereby incorporates herein by reference, U.S. Provisional Patent Application No. 62/263,309, filed 4 Dec. 2015, of the same title as shown above.

FIELD OF THE INVENTION

This invention relates to a specific substrate, for use in growing particularly engineered mushrooms, especially medicinal mushrooms.

BACKGROUND OF THE INVENTION

At this writing, states and commonwealths throughout the United States are debating and otherwise vetting (and in some cases approving) legislation concerning marijuana, generally his sativa. In lay discussions in the media and elsewhere, however, with widespread characterizations such as "medicinal marijuana" and "recreational marijuana," there has been to date an under-emphasis on the important difference between tetrahydrocannabinol (THC) and cannabidiol (CBD), both as to psychogenic as, well as to medicinal effects. The present inventors believe this, will change rapidly, however, as more and more individuals begin to understand that CBD is a non-intoxicating cannabis compound that has important therapeutic properties, that can and should be administered either without accompanying THC for medicinal purposes or in a ratio with THC that is deliberately engineered. Even across all available cannabis strains at this writing, CBD usually accounts for at least 40% of an extract of Cannabis, and there are already known strains of cannabis that are very high in CBD content while also having little or no THC. Thoughtful practitioners of health and therapeutic supplementation therefore understand that the debate is not "marijuana or no marijuana?" but—what are the best sources of CBD and how is it best administered, in what dose or dosage range, in what if any ratio with THC, and—with which excipients?

In parallel to the importance of CBD (or carefully chosen CBD:THC ratios) for therapeutic purposes, medicinal mushrooms continue to play an important role in traditional Chinese herbalism, naturopathic medicine and nutritional therapies both in the United States and abroad. Mushrooms are considered to be one of the richest sources of natural antibiotics, with various species of fungi inhibiting the growth of a wide diversity of microorganisms (Vazirian, M. et al., "Antimicrobial effect of the Lingzhi or Reishi medicinal mushroom *Ganoderma lucidum* (higher Basidiomycetes) and its main compounds," *Int. J. Med. Mushrooms,* 2014; 16(1): 77-84), *Ganoderma lucidum*, a well-known medicinal mushroom, has many pharmacological and biological activities including an antimicrobial effect. (Ibid.). The maitake mushroom (*Grifola frondosa*) contains grifolan, an important beta-glucan polysaccharide, that has been shown to activate macrophages, an important component of the immune system.

Laboratory studies have shown that maitake extract can block the growth of cancer tumors and boost the immune function of mice with cancer. It has also been found that shiitake mushrooms possess beneficial properties. A specific amino acid in shiitake helps speed up the processing of cholesterol in the liver. Shiitake also appears to be a formidable cancer fighter. A polysaccharide compound called lentinan has been isolated from shiitake, too, and in laboratory trials, lentinan appears to stimulate immune-system cells to clear the body of tumor cells. Shiitake appears to be effective against some of the more serious viruses, such as HIV and hepatitis B. Reishi mushrooms have been used in China and Japan for years as a medicine for liver disorders, hypertension, and arthritis, and researchers including Vazirian et al., above, have found that reishi has anti-allergic, anti-inflammatory, anti-viral, anti-bacterial, and antioxidant properties. In vitro experiments also indicate that reishi may help fight cancerous tumors.

Heretofore, to our knowledge, no one has made a sophisticated investigation into the conjunction of medicinal mushrooms and CBD.

In the commercial method of producing mushrooms, a suitably prepared substrate is impregnated with mushroom spores or previously collected mushroom mycelia. Under sterile lab conditions, the spores or mycelia are injected into the substrate, which has been prepared by soaking it in water and sterilizing it. Mycelia are the filamentous hyphen of a mushroom that collect water and nutrients to enable mushrooms to grow. The inoculated substrate is incubated to promote full colonization of the mycelia, at which point the mycelia-laced substrate is referred to as "spawn." Spawning is usually done in a plurality of individual spawn growth vessels or "bags". The substrate provides the nutrients necessary for mycelium growth. The mycelium-impregnated substrate is then allowed to develop under carefully controlled conditions of temperature and moisture, until the hyphen of the mycelium have permeated the substrate. This process usually takes anywhere from three to nine weeks for the mycelium to fully colonize the spawn bag. The spawn bag is allowed to continue to grow until the mycelium enriched product can be harvested between four to 10 weeks from the beginning of the process. Typically, mushroom growers purchase spawn or grow it themselves from agar plates, as will be known to one skilled in the art. In the commercial production of medicinal mushrooms, the spawn bag contains the final product, which is then sold or the contents processed into dry powdered product.

The idea of promoting enhanced uptake, as well as enhanced mycelium growth, by engineering improved substrates is disclosed, for example. In U.S. Pat. No. 7,178,285, "Functional Substrates for Growth of Culinary and Medicinal Mushrooms." In the context of U.S. Pat. No. 7,178,285, one skilled in the art learned to maximize the uptake of desired constituents from the growth medium into the mycelium. U.S. Pat. No. 6,747,065 describes methods of producing mushroom mycelia rich in trace minerals by culturing the mycelia in a broth to which supplements have been added and, again, the emphasis is on maximizing uptake. However, it is possible that as to certain constituents of a medicinal mushroom, it can be as important to LIMIT uptake of certain desired medicinal compounds as it can be to enhance that uptake.

Accordingly, a need remains not only to converge the worlds of medicinal mushrooms and cannabis but to do so in a way that controlled amounts of CBD and THC, in the desired ratio, appear in medicinal mushrooms grown in association with a reliable source of both compounds.

SUMMARY OF THE INVENTION

In order to meet this need, the present invention is a method of growing (preferably but not necessarily) Basiomycetes mushrooms on a substrate that includes unrefined, live or dried cannabis plants (whole or particulated), preferably those cannabis strains high in CBD and low in THC or containing a preferred ratio thereof, as part or all of the growth medium for the mushrooms. By titrating the type and amount of cannabis plant matter in the growth medium, desired uptake of CBD and THC is surprisingly accomplished in engineerable amounts and ratios. Using the whole or minimally particularized live cannabis plant gives new and unexpected results, in the mushroom substrate, in contrast to including cannabis extracts or other purified or semi-purified cannabis products in the growth medium. It is believed, although the inventors do not intend, to be bound by the following theory, that not only are the THC and CBD more accessible for controlled uptake, coming from a fresh (including responsibly dried) Cannabis constituent in the growth medium, but that also the fresh Cannabis plants themselves provide a surprisingly good substrate base for robust mushroom mycelia growth irrespective of their CBD and THC constituents. The resulting combination of mushroom mycelia and cannabis is believed to enhance the absorption of key constituents within the cannabis as well as infuse the cannabis based substrate with extracellular fungal compounds including but not limited to polysaccharide such as beta glucans, glycoproteins, polysaccharide peptides, proteoglycans, triterpenes, ergosterols and ergothionine.

DETAILED DESCRIPTION OF THE INVENTION

As used herein the term "mushroom biomass" refers to mushroom mycelia, fruiting mbodies, spawn, or other life cycle stage of a mushroom, alone or in combination with each other or in combination with the substrate on which the mushroom is grown, including the functional substrates described herein. "Medicinal mushroom" refers to the varieties of mushrooms grown for their desired medicinal properties compounds, as is known in the art.

As an optional addition to the cannabis plants that make up the present growth substrate, other traditional substrate materials may be admixed with the cannabis plants as desired. Particularly suitable substrates for growing mushrooms include grains having high levels of anthocyanins, as noted by the color of the grain. By way of example, certain varieties of corn such as purple corn and black corn have high levels of anthocyanins. Purple barley and purple or black rice varieties are also known to contain high levels of anthocyanins. However, any other suitable mushroom growth substrate may be mixed with the cannabis plants or plant parts as desired, in the practice of the invention.

Any variety of mushroom will, benefit from the methods of the present invention, although due to the intended end use of the mushrooms the variety must be edible by humans. Suitable varieties include, but are not limited to, *Trametes versicolor, Ganoderma lucidum, Hericium erinaceus, Lentinula edodes, Schizophylium commune, Pleuratus ostreatus, Agaricus blazei, Lentinula edodes, Flammulina velutipes, Grifola frondonsus,* and Ohiocordyceps species. Preferably the mushrooms will derive from the family Basiomycetes.

The substrate is prepared for each individual spawn bag. The spawn bags are designed with a high efficiency particulate air (HEPA) filter and can be autoclave heat sterilized. The HEPA filter on the spawn bag allows the bag to breathe and protects the substrate from contamination. Each spawn bag contains 2-5 pounds of prepared substrate consisting of a batch mix of about 3 pounds whole live cannabis plants or particulated fresh cannabis plants with about 2 pounds water. (Alternatively, grains in the desired amount may be admixed with the cannabis plants in the desired ratio.) The unsealed spawn bags are then pasteurized or autoclave steam sterilized up to a temperature of about 250 degrees F. (at approximately 15 psig) for a period between 45 minutes to eight hours—enough to pasteurize or sterilize the substrate as to microorganisms but not enough to denature the cannabis plants as to their essential structure or components. The cook time is the time that steam is supplied and shutdown to the autoclave. HEPA-filtered clean air is then applied for rapid cool down of the autoclave. The cooking time is determined by monitoring the inner core temperatures of the spawn substrate. Following steam pasteurization or autoclaving to sterilize the substrate, the spawn bags are then inoculated with spawn. The spawn bags are then heat sealed and the bags gently tumbled by hand or machine to evenly distribute the spawn throughout the substrate. Thorough mixing may take a few seconds to a minute. Clean room conditions must be maintained during the process to prevent contamination of the substrate. The spawn bags are allowed to spawn run and mature for a period of about 21-90 days, alter which time the mycelium-enriched spawn bags are harvested. The live (fresh) product can be sold by individual spawn bags without opening (or harvesting) the bags.

If a dry product is desired, the spawn bags are opened and the live product contents are spread out on dryer trays. The product is evenly distributed across the dryer tray with less than about 1" height. The dryer trays are loaded into a dehydration unit including but not limited to freeze drying, air drying, Vacuum dehydration or convection drying. The air temperature of the dryer may be adjusted from ambient room temperature to about 190 degrees F. Usually the air temperatures are set to between 115 to 180 degrees F. and drying, times are automatically set from 16-24 hours. The air temperatures can be set lower, requiring longer dry times. The final dried product is tested to have a less than or equal to about 6% by weight moisture content Each spawn bag initially weighing 5 pounds (water and grain mix) is designed to produce slightly greater than 1 kg of dry product.

The dry product is powdered using a grinder with 40 mesh or finer screen. The powder is then bottled or encapsulated directly or formulated into blends and then bottled of encapsulated. The dry product may also be mixed with other ingredients to be used in foods, functional foods, beverages or cosmetics.

Whereas particular embodiments of this invention have been described above for purposes of illustration, it will be evident to those skilled in the art that numerous variations of the details of the present invention may be made without departing from the invention as defined in the appended claims. Therefore, although the invention has been described with respect to particular methods and constituents, above, the scope of the invention is only to be limited insofar as is set forth in the accompanying claims.

We claim:
1. A process for growing mycelium with cannabis, comprising:
 (a) providing a spawn bag with a high efficiency particulate air (HEPA) filter and that can be autoclave heat sterilized;
 (b) preparing a substrate for said spawn bag by providing a batch mix comprising whole live or recently live cannabis plants or particulated live or recently live cannabis plants in combination with water wherein a desired amount of grain may be added and putting the substrate thus formed into said spawn bag to make an unsealed spawn bag;

(c) pasteurizing or autoclave steam sterilizing said unsealed spawn bag;

(d) subsequently inoculating said spawn bag with mycelium spawn and sealing and tumbling said spawn bag;

(e) maturing said spawn bag to create a mycelium-enriched spawn bag; and (f) harvesting said spawn bag.

2. The process according to claim 1, wherein step (e) further comprises the step of:

(e) maturing said spawn bag for 21-90 days to create a mycelium-enriched spawn bag.

3. The process according to claim 1, wherein after (f) harvesting said spawn bag, (g) the spawn bag contents are dried.

* * * * *